(12) United States Patent
Lyster et al.

(10) Patent No.: US 6,405,081 B1
(45) Date of Patent: Jun. 11, 2002

(54) DAMPED BIPHASIC ENERGY DELIVERY CIRCUIT FOR A DEFIBRILLATOR

(75) Inventors: Thomas D. Lyster, Bothell; Bradford E. Gliner; Daniel J. Powers, both of Issaquah, all of WA (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/299,456

(22) Filed: Apr. 22, 1999

(51) Int. Cl.[7] .................................................. A61N 1/39
(52) U.S. Cl. .................................................. 607/5; 607/7
(58) Field of Search ............................ 607/5–8, 72, 74

(56) References Cited

U.S. PATENT DOCUMENTS

| | | |
|---|---|---|
| 3,211,154 A | 10/1965 | Becker et al. |
| 3,241,555 A | 3/1966 | Caywood et al. |
| 3,706,313 A | 12/1972 | Milani et al. |
| 3,782,239 A | 1/1974 | Bell |

(List continued on next page.)

FOREIGN PATENT DOCUMENTS

| | | |
|---|---|---|
| EP | 0281219 | 9/1988 |
| EP | 0315368 | 5/1989 |
| EP | 0353341 | 2/1990 |
| EP | 0437104 | 7/1991 |
| EP | 0491649 | 6/1992 |
| EP | 0507504 | 10/1992 |
| GB | 2070435 | 9/1981 |
| GB | 2083363 | 3/1982 |
| WO | 93/16759 | 9/1993 |
| WO | 94/21327 | 9/1994 |
| WO | 94/22530 | 10/1994 |

OTHER PUBLICATIONS

Gust H. Brady et al., "Multicenter Comparison of Truncated Biphasic Shocks and Standard Damped Sine Wave Monophasic Shocks for Transthoracic Ventricular Defrillaiton", Nov. 15, 1996, Circulation, vol. 94, No. 10, pp. 2508–2514.

(List continued on next page.)

Primary Examiner—George R. Evanisko

(57) ABSTRACT

A defibrillator capable of delivering a damped biphasic truncated (DBT) defibrillation pulse is provided. An energy storage circuit is coupled across a high voltage switch such as an H-bridge for delivering a defibrillation pulse to the patient through a pair of electrodes. A controller operates to control the entire defibrillation process and detects shockable rhythms from the patient via an ECG front end. The energy storage circuit consists of an energy storage capacitor, a series inductor, a shunt diode, and optionally a resistor in series with the inductor. The controller measures as the patient dependent parameter the time interval between the initial delivery of the defibrillation pulse and the occurrence of the peak current or voltage to determine the first and second phases of the defibrillation pulse to provide for compensation for patient impedance. Other types of patient dependent parameters, measured either before or during delivery of the DBT defibrillation pulse, could be alternatively employed to achieve the impedance compensation.

16 Claims, 6 Drawing Sheets

U.S. PATENT DOCUMENTS

| | | |
|---|---|---|
| 3,860,009 A | 1/1975 | Bell et al. |
| 3,862,636 A | 1/1975 | Bell et al. |
| 3,886,950 A | 6/1975 | Ukkstad et al. |
| 4,023,573 A | 5/1977 | Pantridge et al. |
| 4,168,711 A | 9/1979 | Cannon, III et al. ........ 128/419 |
| 4,328,808 A | 5/1982 | Charbonnier et al. |
| 4,419,998 A | 12/1983 | Heath |
| 4,473,078 A | 9/1984 | Angel |
| 4,494,552 A | 1/1985 | Heath |
| 4,504,773 A | 3/1985 | Suzuki et al. |
| 4,574,810 A | 3/1986 | Lerman |
| 4,595,009 A | 6/1986 | Leinders |
| 4,610,254 A | 9/1986 | Morgan et al. |
| 4,619,265 A | 10/1986 | Morgan et al. |
| 4,637,397 A | 1/1987 | Jones et al. |
| 4,745,923 A | 5/1988 | Winstrom |
| 4,800,883 A | 1/1989 | Winstrom |
| 4,821,723 A | 4/1989 | Baker, Jr. et al. |
| 4,834,100 A | 5/1989 | Charms ...................... 128/419 |
| 4,840,177 A | 6/1989 | Charbonnier et al. |
| 4,848,345 A | 7/1989 | Zenkich |
| 4,850,357 A | 7/1989 | Bach, Jr. |
| 4,953,551 A | 9/1990 | Mehra et al. |
| 4,998,531 A | 3/1991 | Bocchi et al. |
| 5,078,134 A | 1/1992 | Heilman et al. |
| 5,083,562 A | 1/1992 | de Coriolis et al. |
| 5,097,833 A | 3/1992 | Campos |
| 5,107,834 A | 4/1992 | Ideker et al. |
| 5,111,813 A | 5/1992 | Charbonnier et al. |
| 5,111,816 A | 5/1992 | Pless et al. |
| 5,184,616 A | 2/1993 | Weiss ......................... 128/419 |
| 5,199,429 A | 4/1993 | Kroll et al. |
| 5,207,219 A | 5/1993 | Adams et al. |
| 5,215,081 A | 6/1993 | Ostroff |
| 5,222,480 A | 6/1993 | Couche et al. |
| 5,222,492 A | 6/1993 | Morgan et al. |
| 5,230,336 A | 7/1993 | Fain et al. |
| 5,237,989 A | 8/1993 | Morgan et al. |
| 5,249,573 A | 10/1993 | Fincke et al. |
| 5,275,157 A | 1/1994 | Morgan et al. ................ 607/6 |
| 5,306,291 A | 4/1994 | Kroll et al. |
| 5,334,219 A | 8/1994 | Kroll |
| 5,334,430 A | 8/1994 | Ishikaum et al. |
| 5,352,239 A | 10/1994 | Pless |
| 5,370,664 A | 12/1994 | Morgan et al. |
| 5,372,606 A | 12/1994 | Lang et al. |
| 5,385,575 A | 1/1995 | Adams |
| 5,411,525 A | 5/1995 | Swanson et al. |
| 5,411,526 A | 5/1995 | Kroll et al. |
| 5,431,686 A | 7/1995 | Kroll et al. |
| 5,489,293 A | 2/1996 | Pless et al. |
| 5,824,017 A | 10/1998 | Sullivan et al. ................ 607/5 |
| 5,891,173 A | 4/1999 | Brewer .......................... 607/5 |
| 5,899,924 A * | 5/1999 | Brewer et al. .................. 607/5 |
| 5,978,706 A * | 11/1999 | Brewer et al. .................. 607/5 |

OTHER PUBLICATIONS

Alferness, et al "The influence of shock waveforms on defibrillation efficacy" *IEEE Engineering in Medicine and Biology*, pp. 25–27 (Jun. 1990).

Anderson et al. "The efficacy of trapezoidal wave forms for ventricular defibrillation" *Chest* 70(2):298–300 (1976).

Blilie et al. "Predicting and validating cardiothoracic current flow using finite element modeling" *PACE* 15:563, Abstract 219 (Apr. 1992).

Chapman et al. "Non–thoracotomy internal defibrillation: Improved efficacy with biphasic shocks" *Circulation* 76312, Abstract No. 1239 (1987).

Cleland "A conceptual Basis for Defibrillation Waveforms" *PACE* vol. 19, pp. 1186–1195 (Aug. 1996).

Cooper et al. "The effect of temporal separation of phases on biphasic waveform defibrillation efficacy" The Annual International Conference of the IEEE Engineering in Medicine and Biology 13(2):0766–0767 (1991).

Crampton et al. "Low energy ventricular defibrillation and miniature defibrillators" *JAMA* 235(21):2284 (1976).

Dahback et al. "Ventricular defibrillation with square waves" *The Lancet* (Jul. 2, 1966).

Echt et al. "Biphasic waveform is more efficacious than monophasic waveform for transthoracic cardioversion" *PACE* 16:914, Abstract No. 256 (Apr. 1993).

Feeser et al. "Strength–duration and probability of success curves for defibrillation with biphasic waveforms" *Circulation* 82(6):2128–2141 (1990).

Guse et al. "Defibrillation with low voltage using a left ventricular catheter and four cutaneous patch electrodes in dogs" *PACE* 14:443–451 (Mar. 1991).

Jones et al. "Decreased defibrillator–induced dysfunction with biphasic rectangular waveforms" *Am. J. Physiol.* 247:H792–796 (1984).

Jones et al. "Defibrillator waveshape optimization" *Devices and Tech Meeting* NIH (1982).

Jones et al. "Improved defibrillator waveform safety factor with biphasic waveforms" *Am. J. Physiol.* 245:H60–65 (1983).

Jones et al. "Reduced excitation threshold in potassium depolarized myocardial cells with symmetrical biphasic waveforms" *J. Mol Cell. Cardiol.* 17(39):XXVII, Abstract No. 39 (1985).

Jude et al. "Fundamental of cardiopulmonary resuscitation" F.A. Davis & Company, Philadelphia, PA, pp. 98–104 (1965).

Kerber et al. "Energy, current and success in defibrillation and cardioversion: clinical studies using an automated impedance–based method of energy adjustment" *Circulation* 77(5):1038 (May 1988).

Kidwai, et al. "Rounded Biphasic Waveform has a Lower Threshold for Transthoracic Ventricular Defibrillation" NASPE Abstract, *PACE* vol. 22, p. 872 Abst. 688 (Apr. 1999).

Knickerbocker et al. "A portable defibrillator" *IEEE Trans on Power and Apparatus Systems* 69:1089–1093 (1963).

Kuowenhoven "The development of the defibrillator" *Annals of Internal Medicine* 71(3):449–458 (1969).

Langer et al. "Considerations in the development of the automatic implantable defibrillator" *Medical Instrumentation* 10(3):163–167 (1976).

Lerman et al. "Current–based versus energy–based ventricular defibrillation: A prospective study" *JACC*.

Lindsay et al. "Prospective evaluation of a sequential pacing and high energy bi–directional shock algorithm for transvenous cardioversion in patients with ventricular tachycardia" *Circulation* 76(3):601–609 (1987).

Mirowski et al. "Clinical treatment of life threatening ventricular tachyarrhythmias with the automatic implantable defibrillator" *American Heart J.* 102(2):265–270 (1981).

Mirowski et al. "Termination of malignant ventricular arrhythmias with an implanted automatic defibrillator in human beings" *New Engl J. Med.* 303(6):322–324 (1980).

Podolsky "Keeping the beat alive" *U.S. News & World Report* (Jul. 22, 1991).

Product Brochure First Medic Semi–Automatic Defibrillators (1994), Spacelabs Medical Products, 15220 N.E. 40$^{th}$ Street, P.O. Box 97013, Redmond, Washington.

Product Brochure for the Shock Advisory System (1987), Physio–Control, 11811 Willow Road Northeast, P.O. Box 97006, Redmond, WA 98703–9706.

Redd (editor), "Defibrillation with biphasic waveform may increase safety, improve survival" *Medlines* pp. 1–2 (Jun.–Jul. 1984).

Saksena et al. "A prospective evaluation of single and dual current pathways for transvenous cardioversion in rapid ventricular tachycardia" *PACE* 10:1130–1141 (Sep.–Oct. 1987).

Saksena et al. "Development for future implantable cardioverters and defibrillators" *PACE* 10:1342–1358 (Nov.–Dec. 1987).

Schuder "The role of an engineering oriented medical research group in developing improved methods and devices for achieving ventricular defibrillator: The University of Missouri experience" *PACE* 16:95–124 (Jan. 1993).

Schuder et al. "A multielectrode–time sequential laboratory defibrillator for the study of implanted electrode systems" *Amer. Soc. Artif. Int. Organs* XVIII:514–519 (1972).

Schuder et al. "Defibrillation of 100 kg calves with asymmetrical, bi–direction, rectangular pulses" *Card. Res.* 18:419–426 (1984).

Schuder et al. "Development of automatic implanted defibrillator" *Devices & Tech Meeting NIH* (1981), Schuder et al. "Transthoracic ventricular defibrillation in the 100 kg calf with symmetrical one–cycle bidirectional rectangular wave stimuli" *IEEE Trans. BME* 30(7):415–422 (1983).

Schuder et al. "Transthoracic ventricular defibrillation with Square–wave stimuli; one–half cycle" *Cir. Res.* XV:258–264 (1964).

Schuder et al. "Ultrahigh–energy hydrogen thratron/SCR bidirectional waveform defibrillator" *Med. & Bio. Eng. & Comput.* 20:419–424 (1982).

Schuder et al. "Waveform dependency in defibrillating 100 kg calves" *Devices & Tech. Meeting* NIH (1982).

Schuder et al. "Waveform dependency in defibrillation" *Devices & Tech Meeting NIH* (1981).

Stanton et al. "Relationship between defibrillation threshold and upper limit of vulnerability in humans" *PACE* 15:563, Astract 221 (Apr. 1992).

Tang et al. "Strength duration curve for ventricular defibrillation using biphasic waveforms" *PACE*, 10: Abstract No. 49 (1987).

Tang et al. "Ventricular defibrillation using biphasic waveforms of different phasic duration" *PACE* 10: Abstract No. 47 (1987).

Tang et al. "Ventricular defibrillation using biphasic waveforms: The importance of phasic duration" *JACC* 13(1):207–214 (1989).

Walcott et al. "Comparison of monophasic, biphasic, and the edmark waveform for external defibrillation" *PACE* 15:563, Abstract 218 (Apr. 1992).

Wathen et al. "Improved defibrillation efficacy using for nonthoracotomy leads for sequential pulse defibrillation" *PACE* 15:563, Abstract 220 (Apr. 1992).

Wetherbee et al. "Subcutaneous patch electrode—A means to obviate thoracotomy for implantation of the automatic cardioverter defibrillation system?" *Circ*, 72:384, Abstract No. 1536 (1985).

Winkle et al. "The implantable defibrillator in ventricular arrhythmias" *Hispital Practive*, pp. 149–165 (Mar. 1983).

Winkle et al. "Improved low energy defibrillation efficacy in man using a biphasic truncated exponential waveform" *JACC* 9(2):142A (1987).

Zipes "Sudden cardiac death" *Circulation* 85(1):160–166 (1992).

\* cited by examiner

DAMPED BIPHASIC ENERGY DELIVERY CIRCUIT FOR A DEFIBRILLATOR

BACKGROUND OF THE INVENTION

This invention relates to electrotherapy circuits and in particular to a defibrillator which is capable of applying damped biphasic defibrillation pulses to a patient.

Electro-chemical activity within a human heart normally causes the heart muscle fibers to contract and relax in a synchronized manner that results in the effective pumping of blood from the ventricles to the body's vital organs. Sudden cardiac death is often caused by ventricular fibrillation (VF) in which abnormal electrical activity within the heart causes the individual muscle fibers to contract in an unsynchronized and chaotic way. The only effective treatment for VF is electrical defibrillation in which an electrical shock is applied to the heart to allow the heart's electrochemical system to re-synchronize itself. Once organized electrical activity is restored, synchronized muscle contractions usually follow, leading to the restoration of cardiac rhythm.

FIG. 1 is an illustration of a defibrillator 10 being applied by a user 12 to resuscitate a patient 14 suffering from cardiac arrest. In cardiac arrest, otherwise known as sudden cardiac arrest, the patient is stricken with a life threatening interruption to their normal heart rhythm, typically in the form of ventricular fibrillation (VF) or ventricular tachycardia (VT) that is not accompanied by a palpable pulse (shockable VT). In VF, the normal rhythmic ventricular contractions are replaced by rapid, irregular twitching that results in ineffective and severely reduced pumping by the heart. If normal rhythm is not restored within a time frame commonly understood to be approximately 8 to 10 minutes, the patient 14 will die. Conversely, the quicker defibrillation can be applied after the onset of VF, the better the chances that the patient 14 will survive the event. The defibrillator 10 may be in the form of an automatic external defibrillator (AED) capable of being used by a first responder. The defibrillator 10 may also be in the form of a manual defibrillator for use by paramedics or other highly trained medical personnel.

A pair of electrodes 16 are applied across the chest of the patient 14 by the user 12 in order to acquire an ECG signal from the patient's heart. The defibrillator 10 then analyzes the ECG signal to detect ventricular fibrillation (VF). If VF is detected, the defibrillator 10 signals the user 12 that a shock is advised. After detecting VF or other shockable rhythm, the user 12 then presses a shock button on the defibrillator 10 to deliver defibrillation pulse to resuscitate the patient 14.

The patient 14 has a transthoracic impedance ("patient impedance") that spans a range commonly understood to be 20 to 200 ohms. It is desirable that the defibrillator 10 provide an impedance-compensated defibrillation pulse that delivers a desired amount of energy to any patient across the range of patient impedances and with a peak current limited to safe levels substantially less than a maximum value.

The minimum amount of patient current and energy delivered that is required for effective defibrillation depends upon the particular shape of the defibrillation waveform, including its amplitude, duration, shape (such as sine, damped sine, square, exponential decay). The minimum amount of energy further depends on whether the current waveform has a single polarity (monophasic), both negative and positive polarities (biphasic) or multiple negative and positive polarities (multiphasic).

If the peak current of the defibrillation pulse that is delivered to the patient 14 exceeds the maximum value, damage to tissue and decreased efficacy of the defibrillation pulse will likely result. Peak current is the highest level of current that occurs during delivery of the defibrillation pulse. Limiting peak currents to less than the maximum value in the defibrillation pulse is desirable for both efficacy and patient safety.

Most external defibrillators use a single energy storage capacitor charged to a fixed voltage level resulting in a broad range of possible discharge times and tilt values of the defibrillation pulse across the range of patient impedances. A method of shaping the waveform of the defibrillation pulse in terms of duration and tilt is discussed in U.S. Pat. No. 5,607,454, "Electrotherapy Method and Apparatus", issued Mar. 4, 1997 to Gliner et al. Using a single capacitor to provide the defibrillation pulse at adequate energy levels across the entire range of patient impedances can result in higher than necessary peak currents being delivered to patients with low patient impedances. At the same time, the charge voltage of the energy storage capacitor must be adequate to deliver a defibrillation pulse with the desired amount of energy to patients with high patient impedances.

Various prior art solutions to the problem of high peak currents exist using resistance placed in series with the patient 14 to compensate for variations in patient impedance. In U.S. Pat. No. 5,514,160, "Implantable Defibrillator For Producing A Rectangular-Shaped Defibrillation Waveform", issued May 7, 1996, to Kroll et al., an implantable defibrillator having a rectilinear-shaped first phase uses a MOSFET operating as a variable resistor in series with the energy storage capacitor to limit the peak current. In U.S. Pat. No. 5,733,310, "Electrotherapy Circuit and Method For Producing Therapeutic Discharge Waveform Immediately Following Sensing Pulse", issued Mar. 31, 1998, to Lopin et al., an electrotherapy circuit senses patient impedance and selects among a set of series resistors in series with the energy storage capacitor to create a sawtooth approximation to a rectilinear shape in the defibrillation pulse. Using current limiting resistors to limit peak current as taught by the prior art results in substantial amounts of power being dissipated in the resistors which increases the energy requirements on the defibrillator battery. Furthermore, such prior art circuits require complex, active control systems to regulate the current during the delivery of the defibrillation pulse.

The use of inductors in the energy storage circuit along with the energy storage capacitor to shape the defibrillation pulse is well known in the art. The basic RLC defibrillator topology is explained in U.S. Pat. No. 4,168,711, "Reversal Protection for RLC Defibrillator", issued Sep. 25, 1979 to Cannon, III et al. RLC defibrillators utilize an inductor in series with the energy storage capacitor to deliver a damped sine wave defibrillation pulse. Such waveforms are typically not truncated and the discharge time is on the order of 50–60 milliseconds (ms). RLC defibrillator designs according to the prior art do not address the problem of limiting peak currents or otherwise compensating for the range of patient impedances.

More recent biphasic defibrillator designs such as the Heartstream Forerunner® automatic external defibrillator (AED) utilize solid state switches such as silicon controlled rectifiers (SCRs) and insulated gate bipolar transistors (IGBTs) connected in an H-bridge to produce a biphasic truncated exponential (BTE) defibrillation pulse. Such solid state switches require snubber circuits in series with the energy storage capacitor to control the rate of change of voltage or current through the switches to prevent switch damage as well as to prevent false triggering from transient energy. The snubber circuit in the Forerunner AED employs a 150 microHenry (uH) inductor. Similarly, in U.S. Pat. No. 5,824,017, "H-Bridge Circuit For Generating A High-Energy Biphasic Waveform In An External Defibrillator", issued Oct. 20, 1998, to Sullivan et al., a protective element having resistive and inductive properties is interposed between the energy storage capacitor and the H bridge. Sullivan et al teach that the protective element 27 is used to the limit the rate of change of voltage across, and current flow to, the SCR switches of the H bridge. However, snubber circuits, while designed to protect the switch components of the H-bridge, do not address the problem of limiting peak current to the patient across the range of patient impedances.

It would therefore be desirable to provide a defibrillator that delivers an impedance-compensated defibrillation pulse to the patient with limited peak currents.

SUMMARY OF THE INVENTION

A defibrillator capable of delivering a current-limited defibrillation pulse is provided. An energy storage circuit is charged to a high voltage by a high voltage charger circuit which receives its energy from a battery. The energy storage circuit is coupled across a high voltage switch such as an H-bridge for delivering a defibrillation pulse to the patient through a pair of electrodes. A controller operates to control the entire defibrillation process and detects shockable rhythms from the patient via an ECG front end.

The energy storage circuit consists of an energy storage capacitor, a series inductor, a shunt diode, and optionally a resistor in series with the inductor. The series inductor has an inductance value chosen to limit the peak current of the defibrillation pulse delivered to the patient for the lowest expected value of patient impedance. The inductance value is chosen as a function of the capacitance value and charge voltage of the energy storage capacitor. The series resistor may be added depending on the internal resistance of the series inductor. Alternatively, the series inductor may be modeled as an ideal inductor and the series resistor represents the effective series resistance (ESR) of the series inductor. The shunt diode is necessary to clamp the voltage generated by the energy stored in the series inductor because the defibrillation pulse is truncated by the high voltage switch. The waveform developed according to the present invention is a damped biphasic truncated (DBT) waveform which is distinct from the biphasic truncated exponential (BTE) waveform of the prior art.

The controller uses the current and voltage information supplied by the energy storage circuit to determine a patient dependent parameter. In the preferred embodiment, the patient dependent parameter is measured during the delivery of the defibrillation pulse. Alternatively, the patient dependent parameter may be measured before delivery of the defibrillation by the use of a low level signal or the delivery of a non-therapeutic pulse to the patient.

A patient dependent parameter is a measurement of time, voltage or current that is directly related to the patient impedance for the given combination of capacitance, inductance, and series resistance. This patient dependent parameter can be used by the controller to set the time of the first and second phases of the defibrillation pulse to control the amount of energy delivered to the patient. One such patient dependent parameter that can be determined in the case of the DBT defibrillation pulse is the measured time interval between the initial delivery of the defibrillation pulse to the time that the current or the voltage peaks. Other patient dependent parameters, such as the percentage voltage drop across the patient, percentage voltage drop across the energy storage capacitor, or measured time to reach a circuit charge delivery using a current integrator, may also be effectively used.

One feature of the present invention is to provide a defibrillator that delivers current limited defibrillation pulses.

A further feature of the present invention is to provide a defibrillator that delivers damped biphasic truncated (DBT) defibrillation pulses.

Another feature of the present invention is to provide an energy storage circuit capable of delivering current limited defibrillation pulses.

A further feature of the present invention is to provide a method of delivering damped biphasic truncated defibrillation pulses.

Other features, attainments, and advantages will become apparent to those skilled in the art upon a reading of the following description when taken in conjunction with the accompanying drawings.

DETAILED DESCRIPTION OF THE INVENTION

Figure 1:
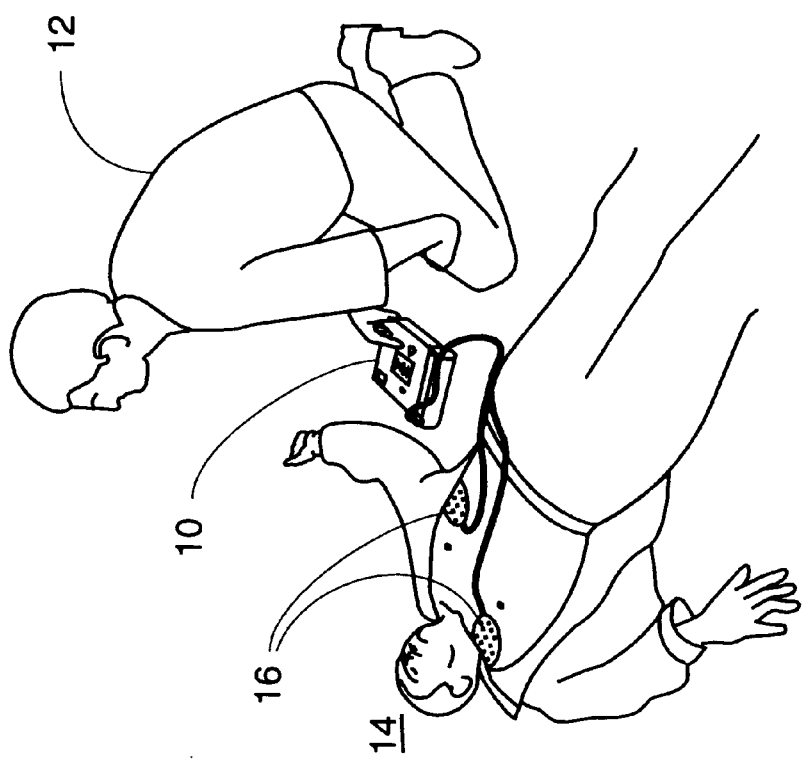
FIG. 1 is an illustration of a defibrillator being applied by a user to resuscitate a patient suffering from cardiac arrest.
Figure 2:
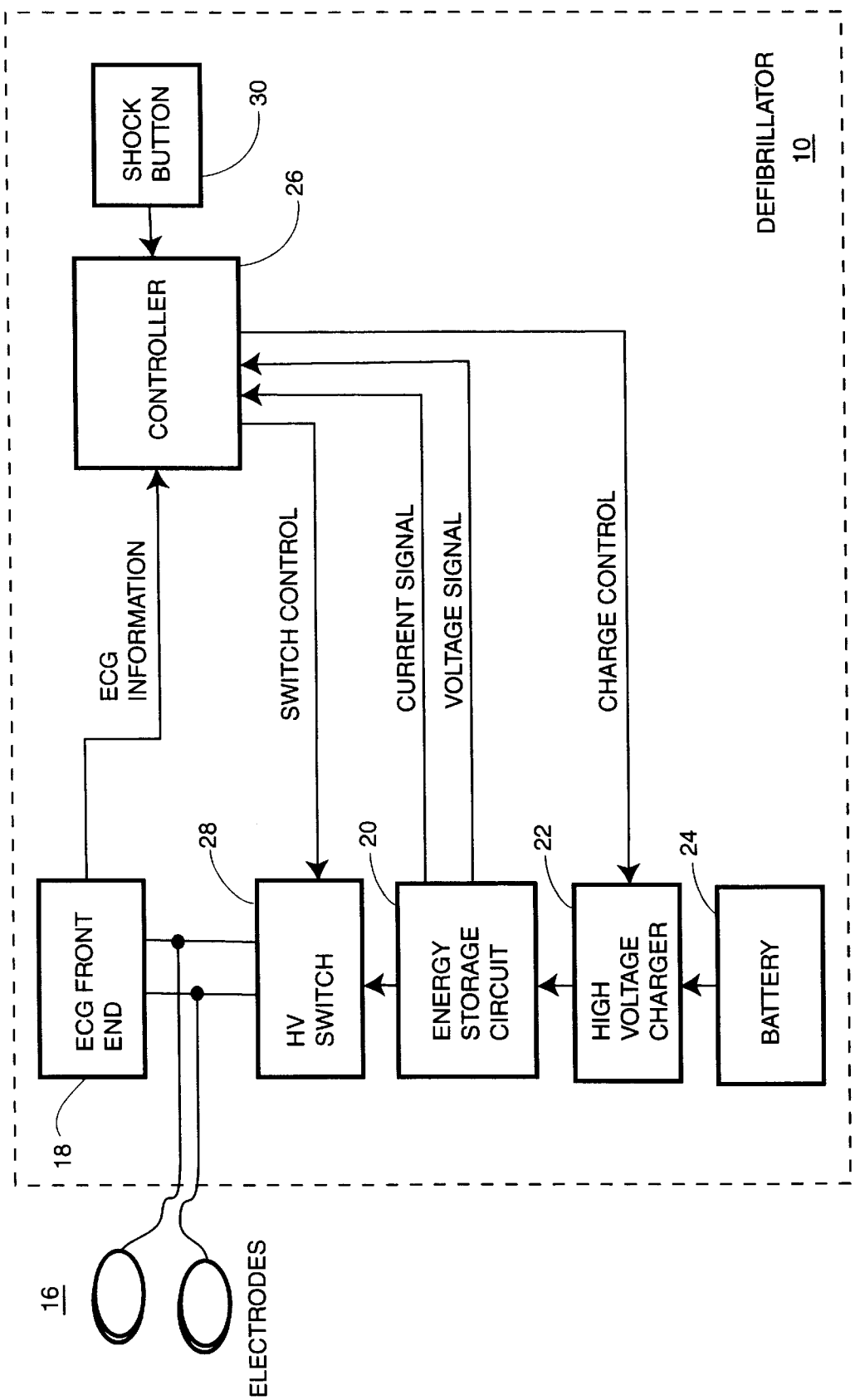
FIG. 2 is a simplified block diagram of a defibrillator according to the present invention.

FIG. 2 is a simplified block diagram of a defibrillator 10 according to the present invention. The pair of electrodes 16 for coupling to the patient 14 are connected to an ECG front end 18 and further connected to an HV switch 28. The ECG front end 18 provides for detection, filtering, and digitizing of the ECG signal from the patient 14. The ECG signal is in turn provided to a controller 26 which runs a shock advisory algorithm that is capable of detecting ventricular fibrillation (VF) or other shockable rhythm that is susceptible to treatment by electrotherapy.

A shock button 30, typically part of a user interface of the defibrillator 10 allows the user to initiate the delivery of a defibrillation pulse through the pair of electrodes 16 after the controller 26 has detected VF or other shockable rhythm. A battery 24 provides power for the defibrillator 10 in general and in particular for a high voltage charger 22 which charges the capacitors in an energy storage circuit 20. Typical battery voltages are 12 volts or less, while the energy storage circuit 20 may be charged to 1500 volts or more. A charge voltage control signal from the controller 26 determines the charge voltage in the energy storage circuit 20.

The energy storage circuit 20 is connected to the HV switch 28 which operates to deliver the defibrillation pulse across the pair of electrodes 16 to the patient 14 in the desired polarity and duration response to the switch control signal from the controller 26. The HV switch 28 is constructed using an H bridge to deliver biphasic defibrillation pulses in the preferred embodiment but could readily be adapted to deliver monophasic or multiphasic defibrillation pulses and still realize the benefits of the present invention.

Figure 3:
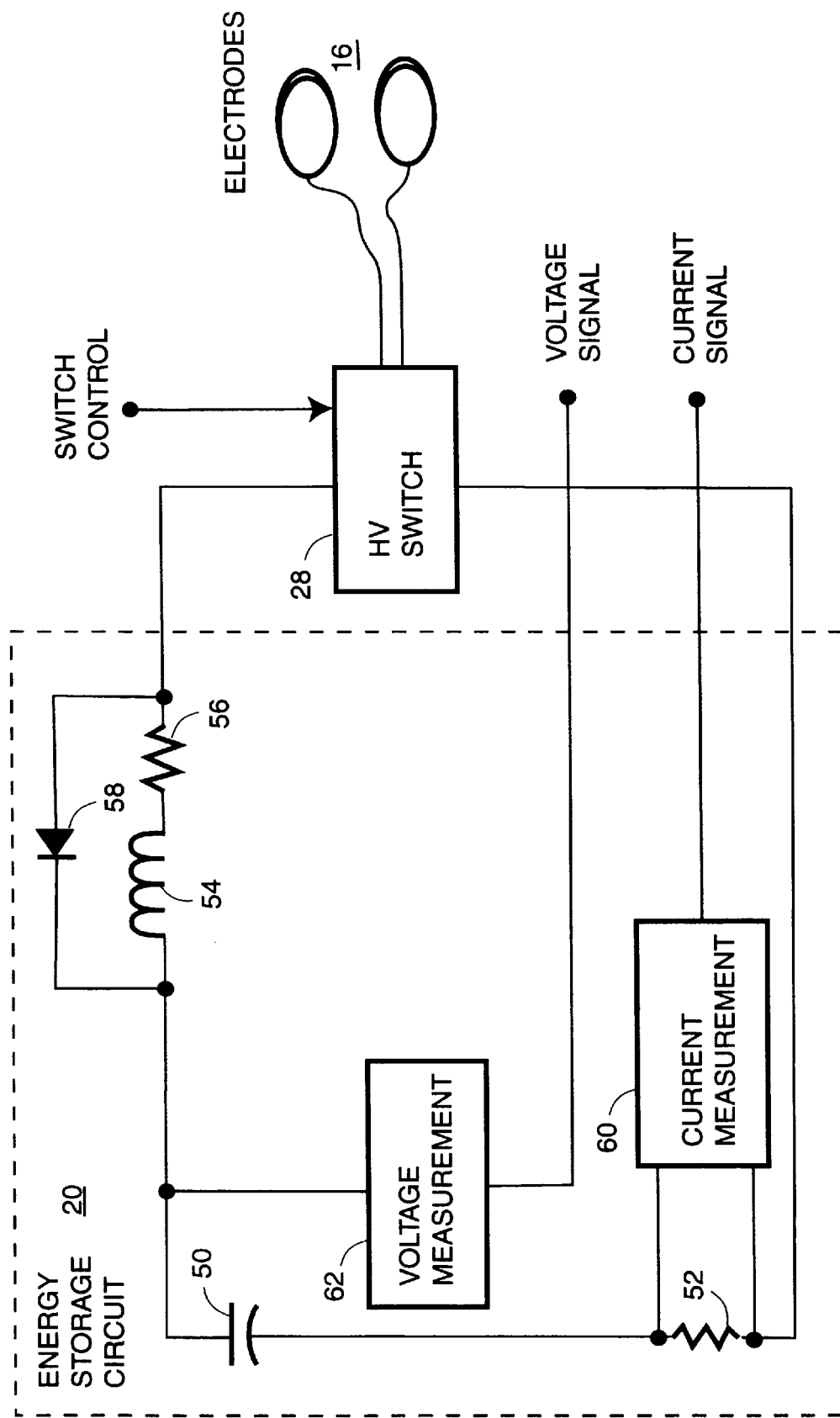
FIG. 3 is a schematic diagram of the energy storage circuit of the defibrillator of FIG. 2.

In FIG. 3, there is shown a simplified schematic of the energy storage circuit 20. An energy storage capacitor 50 stores the energy for the defibrillation pulse and is typically charged to over 2,000 volts in the preferred embodiment. The energy storage capacitor 50 is connected to the HV switch 28 through a current sense resistor 52 on one lead and through a series inductor 54 and series resistor 56 on the other lead. A shunt diode 58 is coupled in shunt across the series inductor 54 and series resistor 56. The HV switch 28 connects the energy storage circuit 20 to the pair of electrodes 16 in a selected polarity and for a selected duration responsive to the switch control signal from the controller 26. The shunt diode 58 is necessary to include in the energy storage circuit 20 because the defibrillation pulse is truncated, leaving a sudden interruption in the current path. The shunt diode 58 becomes forward biased upon truncation in order to shunt the voltage generated by the energy stored in the series inductor 54.

A voltage measurement circuit 62 is connected across the energy storage capacitor 50 to measure the charge voltage and provide a voltage signal back to the controller 26. The voltage measurement circuit 62 could be implemented using a voltage divider network to scale the voltage down to a lower level signal that is then supplied to an analog to digital converter (ADC) which provides the voltage signal to the controller 26 in the form of digital measurement values.

A current measurement circuit 60 is connected across the current sense resistor 52 to measure the current flowing from the energy storage capacitor 50. The current sense resistor 52 has a relatively small resistance value that does not interfere with operation of the energy storage circuit 20. The current measurement circuit 60 may include an ADC to provide the current signal to the controller 26 in the form of digital measurement values. The current measurement circuit 60 may also include an integrator circuit to determine the amount of charge that has been discharged from the energy storage capacitor 50 if required for measuring a patient dependent parameter. Such an integrator could be an analog integrator constructed using well known techniques using operational amplifiers and capacitors. Depending on the method of measuring a patient dependent parameter used for controlling the first and second phase durations of the defibrillation pulse, either the voltage measurement circuit 62 or the current measurement circuit 60 could be omitted from the energy storage circuit 20. The use of the DBT defibrillation pulse according to the present invention allows for a selected energy level, such as 150 joules, to be delivered with an acceptable level of accuracy, to a patient of unknown impedance within the range of 20 to 200 ohms, and with both pulse duration and peak current within predetermined limits.

The choice of capacitance value and charge voltage for the energy storage capacitor 50, inductance value for the series inductor 54, and resistance value for the series resistor 56 to achieve the DBT defibrillation pulse with the desired characteristics requires a reasonable amount of experimentation. The DBT defibrillation pulse must have the desired limit on peak current for low patient impedances. At the same time, the DBT defibrillation pulse should provide an adequate time duration between the initialization of the defibrillation pulse and the peak current or peak voltage to allow for accurate measurement of the patient dependent parameter if that patient dependent parameter is chosen for the control method.

The following tables provide the results of various combinations of component values and charge voltages that could be chosen to achieve a DBT defibrillation pulse.

TABLE 1

Combinations of Component Values

| Combination | R series (ohms) | L series (mH) | Capacitance (uF) | Charge Voltage (V) | Stored Energy (J) |
|---|---|---|---|---|---|
| 1 | 10 | 10 | 100 | 1800 | 160 |
| 2 | 10 | 20 | 100 | 1800 | 160 |
| 3 | 10 | 20 | 70 | 2150 | 160 |
| 4 | 20 | 20 | 70 | 2300 | 185 |

TABLE 2

Peak current and energy delivered for each combination from Table 1.

| Patient Impedance | Combination 1 | Combination 2 | Combination 3 | Combination 4 |
|---|---|---|---|---|
| 25 ohms | | | | |
| Peak Current (A) | 44 | 41 | 46 | 41 |
| Energy Delivered (J) | 108 | 108 | 109 | 96.7 |
| 50 ohms | | | | |
| Peak Current (A) | 28 | 27 | 31 | 29 |
| Energy Delivered (J) | 127 | 127 | 127 | 124.3 |
| 100 ohms | | | | |
| Peak Current (A) | 16 | 15 | 18 | 18 |
| Energy Delivered (J) | 138 | 138 | 138 | 145 |
| 175 ohms | | | | |
| Peak Current (A) | 9.8 | 9.6 | 11.5 | 11.5 |
| Energy Delivered (J) | 144 | 144 | 144 | 156.2 |

All delivered energy calculations assume that approximately 95% of the energy stored in the energy storage capacitor 50 is delivered to the patient 14. Taking combination 4 as an example, omitting the series inductor 54 to obtain a BTE defibrillation pulse would result in substantially higher peak currents of 51 A for the 25 ohm patient impedance and 33 A for the 50 ohm patient impedance compared with 41 A and 29 A respectively according to the DBT defibrillation pulse of the present invention.

The data from Table 2 show that inductance values in the 10 to 20 mH range for the combinations 1–4 deliver acceptable results in limiting peak current for low patient impedances while providing adequate energy delivery for high patient impedances. The inductance value of the series inductor 54 may be in the range of 5 to 100 mH in conjunction with the energy storage capacitor 50 with a capacitance of 50 to 100 uF to achieve the DBT defibrillation pulse according to the present invention. Inductance values less than 5 mH tend to provide insufficient limiting of the peak current to the patient 14. Inductance values greater than 100 mH require inductors that are physically too large for portable defibrillator applications.

Figure 4:
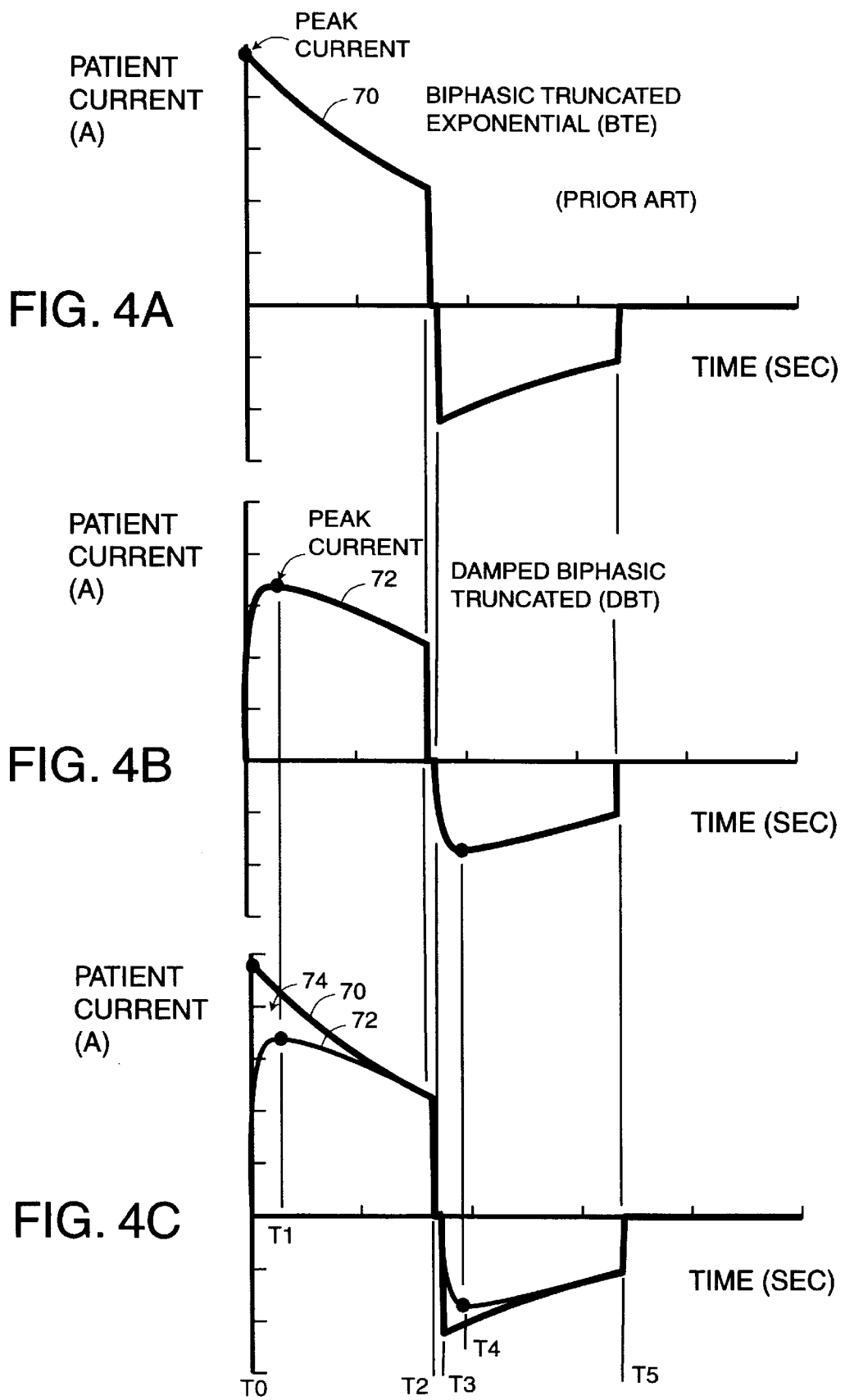
FIGS. 4A–C are graphs comparing the typical waveshapes of a biphasic truncated exponential (BTE) defibrillation pulse generated according to the prior art with the damped biphasic truncated (DBT) defibrillation pulse generated according to the present invention.

FIGS. 4A–C are graphs (not to scale) of patient current versus time from initial delivery of the defibrillation pulse comparing the typical waveshapes of a biphasic truncated exponential (BTE) defibrillation pulse generated according to the prior art with the damped biphasic truncated (DBT) defibrillation pulse generated according to the present invention.

In FIG. 4A, there is shown a graph of a typical BTE waveform drawn as trace 70. In the first phase spanning time T0 to T2, the peak current occurs at or very close to time T0, with an exponential decay in the patient current that is truncated at time T2. Truncation means that the defibrillation pulse is switched off while a substantial amount of current is continuing to flow to the patient 14. The second phase spans from time T3 to T5 with a peak current at or very close to time T3 followed by exponential decay to time T5 where the second phase is truncated.

In FIG. 4B, there is shown a graph of a typical DBT waveform according to the present invention drawn as trace 72. The truncation times T2 and T5 are aligned for reasons of comparison to show how the BTE and DBT waveforms are roughly equivalent in the amount of energy delivered. In the first phase, the peak current now occurs at time T1 which is substantially later than time T0 and at a value substantially less than peak current of the BTE waveform of FIG. 4A. The decay is no longer exponential and substantially flatter than the BTE waveform. Similarly in the second phase, the peak current occurs at time T4 which is substantially later than time T3 and at a value substantially less than the peak current at time T3 of the BTE waveform.

In FIG. 4C, there is shown a graph of the traces 70 and 72 superimposed on each other to visually compare the BTE and DBT waveshapes. It has been discovered that the area 74 between the traces 70 and 72 which represents the energy delivered in the peak current has relatively little therapeutic value to the patient 14. This energy is therefore wasted and a potentially harmful to the patient 14 if the peak current of the BTE waveform exceeds the maximum value. Limiting the peak current according to the present invention may have the additional advantage of allowing the use of higher charge voltages on the energy storage capacitor 50 while decreasing its capacitance value creates advantages in terms of reduced physical size and weight.

Figure 5:
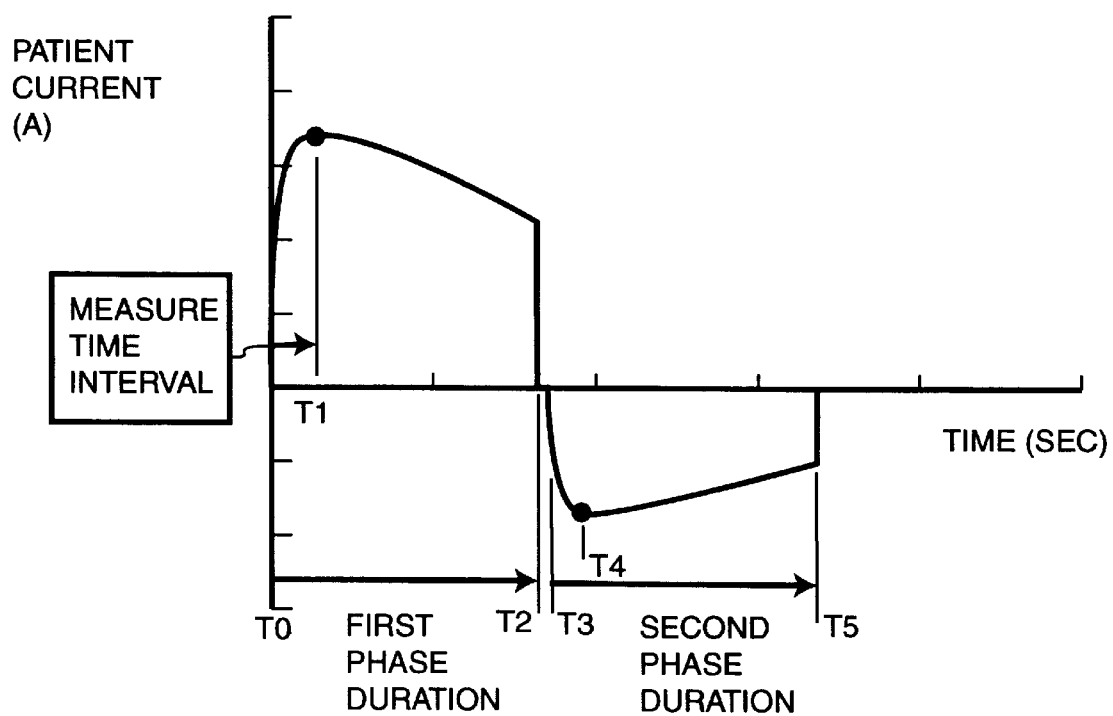
FIG. 5 is a graph of the DBT defibrillation pulse generated according the present invention.

In FIG. 5, there is shown a graph of a typical DBT waveshape illustrating a method of controlling the durations of the first and second phases. It is well known that the amount of energy delivered by a defibrillation pulse varies by patient impedance and can be controlled by appropriate setting of the duration time of the first and second phases. A patient dependent parameter which correlates with patient impedance can be measured, either before or during the delivery of the defibrillation pulse, and then used to determine the first and second phase durations.

As shown in FIG. 5, a method of controlling the first and second phase durations of the DBT defibrillation can be based on a measurement of the time interval between time T0, the initial delivery of the defibrillation pulse, and time T1, the time that the peak current occurs. The value of this time interval directly depends on the patient impedance which can then be used as a patient dependent parameter to determine the first phase duration spanning time T0 to T2 and the second phase duration spanning time T3 to T5. It will be noted that this method will work equally well by measuring the voltage across the pair of electrodes 16 and measuring the time interval to the peak voltage.

In this way, the patient dependent parameter is determined during the delivery of the defibrillation pulse. This method has the advantage of eliminating the separate step of determining the patient dependent parameter prior to delivery of the defibrillation pulse. Measuring the patient dependent parameter prior to delivery of the defibrillation pulse may also be accomplished by using existing circuitry which detects patient contact across the pair of electrodes 16 and still gain the advantages of the DBT defibrillation pulse according to the present invention.

Figure 6:
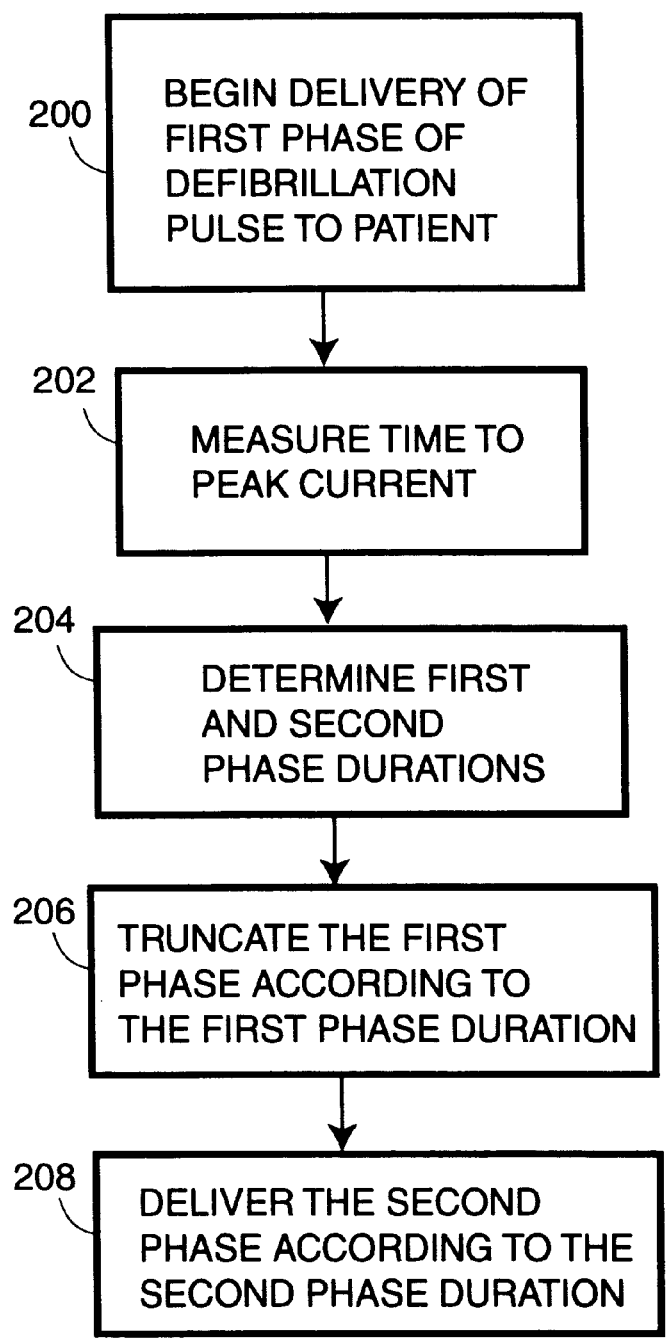
FIG. 6 is a flow diagram of the method of generating a DBT defibrillation pulse according to the present invention.

In FIG. 6 there is shown a flow diagram of a process of delivering an impedance-compensated defibrillation pulse by the defibrillator 10 based on one embodiment of the present invention that addresses the time interval to peak current. Another embodiment which is substantially similar is the time interval to peak voltage.

In step 200 labeled BEGIN DELIVERY OF FIRST PHASE OF DEFIBRILLATION PULSE TO PATIENT, the delivery of the defibrillation pulse is initiated by the controller 26 which controls the HV switch 28 using the switch control signal. In the typical scenario such as in an AED, the pair electrodes 16 have been placed on the patient 14, the controller 26 has detected a shockable rhythm such as VF, and the user 12 has pressed the shock button 30 to deliver the defibrillation pulse. The controller 26 then begins the process of delivering the defibrillation pulse and functions as a control system to provide for the proper sequence of first and second phases and with the phase durations appropriate for the patient impedance of the patient 14.

In an alternative embodiment, the patient dependent parameter would have already been measured prior to the step 200 using, for example, with the ECG front end 18 equipped with circuitry capable of measuring patient impedance either directly or indirectly. A low level test signal or a non-therapeutic pulse could be generated and then measured to obtain the patient dependent parameter before delivery of the DBT defibrillation pulse.

In step 202 labeled MEASURE TIME TO PEAK CURRENT, the controller 26 monitors the current signal during the delivery of the defibrillation pulse and determines the time interval from the initial delivery of the defibrillation pulse to the time of the peak current. On the graph of FIG. 5, these are times T0 and T1 respectively.

In step 204 labeled DETERMINE FIRST AND SECOND PHASE DURATIONS, the time interval from step 202 is used to determine the first and second phase durations. Such a determination can be made using a mathematical formula or more simply by using a look up table containing the phase duration values. The phase duration values would be predetermined for the desired energy level such as 150 joules. As much resolution as needed could be added to the look up table to achieve delivery of the defibrillation pulse according to the desired energy level within specification limits.

In step 206 labeled TRUNCATE THE FIRST PHASE ACCORDING TO THE FIRST PHASE DURATION, the first phase is allowed to continue for the first phase duration that was determined in step 204. It is assumed that the first phase duration is sufficiently long to allow step 204 to complete in order to properly truncate the first phase according to the first phase duration.

In step 208 labeled DELIVER THE SECOND PHASE ACCORDING TO THE SECOND PHASE DURATION, the second phase is delivered over the second phase duration which was determined in step 204. Alternatively, a second time duration measurement which measures the time interval between times T3 and T4 could be made to determine the second time interval in a manner similar to the first time interval.

Other methods of determining the patient dependent parameter during the delivery of the DBT defibrillation pulse may be used. For example, the current measurement circuit 60 could contain the integrator circuit which provides a measurement of integrated current which is a function of total charge delivered to the patient. A time interval measurement could be made of the time to reach a predetermined level of charge which is then used to determine the first and second phase durations. This method is used in the Heartstream Forerunner® defibrillator to control the BTE biphasic waveform and could also be used to control the DBT defibrillation pulse of the present invention.

Another example of determining a patient dependent parameter is to measure the voltage across the energy storage capacitor 50 and truncate the first and second phases when the voltage has dropped to predetermined percentages of the full charge voltage. A further example is to measure the voltage across the pair of electrodes 16 and truncate each phase when the charge voltage across the energy storage capacitor 50 has dropped to a predetermined percentage of a maximum level.

It will be obvious to those having ordinary skill in the art that many changes may be made in the details of the above-described preferred embodiments of the invention without departing from the spirit of the invention in its broader aspects. For example, a wide range of inductance values for the series inductor, resistance values for the series resistor, and capacitance values for the energy storage capacitor may be chosen as long as the DBT defibrillation pulse has a peak current that is sufficiently limited and the time interval from initiation to peak current is sufficiently long to enable an accurate measurement for the control method explained above. Therefore, the scope of the present invention should be determined by the following claims.

What we claim as our invention is:

1. A defibrillator comprising:
   a pair of electrodes for coupling to a patient;
   an HV switch coupled to said pair of electrodes;
   an energy storage circuit for delivering a damped biphasic truncated defibrillation pulse through said HV switch to said patient, said energy storage circuit comprising,
      an energy storage capacitor coupled across said HV switch,
      a series inductor and a series resistor coupled in series with said energy storage capacitor, and
      a shunt diode coupled across said series inductor and series resistor.

2. The defibrillator according to claim 1 wherein said series inductor has an inductance value between 5 and 100 milliHenries.

3. A defibrillator comprising:
   a pair of electrodes for coupling to a patient;
   an HV switch coupled to said pair of electrodes;
   an energy storage circuit for generating a damped biphasic truncated defibrillation pulse, the energy storage circuit including an inductor, a capacitor, and a resistor that is coupled to the inductor and the capacitor;
   a controller coupled to said HV switch and to said energy storage circuit; and
   wherein said controller initiates delivery of said damped biphasic truncated defibrillation pulse, measures a patient dependent parameter, and determines respective durations of first and second phases of said damped biphasic truncated defibrillation pulse based on said patient dependent parameter.

4. The defibrillator according to claim 3 further comprising an ECG front end coupled to said pair of electrodes to provide ECG information to said controller to detect a shockable rhythm.

5. The defibrillator according to claim 3 wherein said controller measures said patient dependent parameter according to a current signal provided to said controller by said energy storage circuit.

6. The defibrillator according to claim 5 wherein said patient dependent parameter comprises a time duration between an initiation of said damped biphasic truncated defibrillation pulse and a peak current generated by said energy storage circuit and determined from said current signal.

7. The defibrillator according to claim 3 wherein said controller measures said patient dependent parameter according to a voltage signal provided to said controller by said energy storage circuit.

8. The defibrillator according to claim 7 wherein said patient dependent parameter comprises a time duration between an initiation of said damped biphasic truncated defibrillation pulse and a peak voltage generated by said energy controller circuit and determined from said voltage signal.

9. The defibrillator according to claim 3 wherein:
   said controller includes a look up table for storing information; and
   said controller determines said first and second phase durations based on said stored information and said patient dependent parameter.

10. The defibrillator according to claim 3 wherein said damped biphasic truncated defibrillation pulse has a peak value that is limited to less than a maximum safe value.

11. The defibrillator of claim 3 wherein the capacitor, inductor, and resistor are in series with one another.

12. The defibrillator of claim 3 wherein the energy storage circuit further includes a diode coupled across the inductor.

13. The defibrillator of claim 3 wherein:
   the inductor and the resistor are in series with one another; and
   the energy storage circuit further includes a diode that is coupled across the series combination of the inductor and resistor.

14. A defibrillator comprising:
   a pair of electrodes for coupling to a patient;
   an HV switch coupled to said pair of electrodes;
   an energy storage circuit for generating a damped biphasic truncated defibrillation pulse, the energy storage circuit including,
      an energy storage capacitor coupled across said HV switch,
      a series inductor and a series resistor coupled in series with said energy storage capacitor, and
      a shunt diode coupled across said series inductor and series resistor; and
   a controller coupled to said HV switch and to said energy storage circuit;
   wherein said controller initiates delivery of said damped biphasic truncated defibrillation, measures a patient dependent parameter, and determines first and second phase durations of said damped biphasic truncated defibrillation pulse based on said patient dependent parameter.

15. The defibrillator according to claim 14 wherein said series inductor has an inductance value between 5 and 100 milliHenries.

16. A defibrillator comprising:

a pair of electrodes for coupling to a patient;

an HV switch coupled to said pair of electrodes; and an LC energy storage circuit for delivering a damped-decay biphasic truncated defibrillation pulse through said HV switch to said patient, said LC energy storage circuit including a capacitor, an inductor, and a resistor in series with the capacitor and inductor.

* * * * *